United States Patent
Kelm (10) Patent No.: US 8,706,320 B2
(45) Date of Patent: Apr. 22, 2014

(54) PARTICLE SENSOR FOR IN SITU ATMOSPHERIC MEASUREMENT

(71) Applicant: Airbus Operations GmbH, Hamburg (DE)

(72) Inventor: Roland Kelm, Hamburg (DE)

(73) Assignee: Airbus Operations GmbH, Hamburg (DE)

( * ) Notice: Subject to any disclaimer, the term of this patent is extended or adjusted under 35 U.S.C. 154(b) by 0 days.

(21) Appl. No.: 13/688,474

(22) Filed: Nov. 29, 2012

(65) Prior Publication Data

US 2013/0110326 A1    May 2, 2013

Related U.S. Application Data (63) Continuation of application No. PCT/EP2011/059226, filed on Jun. 3, 2011.

(60) Provisional application No. 61/351,588, filed on Jun. 4, 2010.

(30) Foreign Application Priority Data

Jun. 4, 2010    (DE) .......................... 10 2010 022 673

(51) Int. Cl.
  *G01N 1/22*    (2006.01)
(52) U.S. Cl.
  USPC .......... 701/3; 73/31.01; 73/31.02; 73/170.16; 340/601; 340/963
(58) Field of Classification Search
  USPC ........ 701/3; 73/31.01, 31.02, 170.16, 170.28; 340/963
  See application file for complete search history.

(56) References Cited

U.S. PATENT DOCUMENTS

| 6,809,648 | B1 | 10/2004 | Fleming |
| 6,941,806 | B2* | 9/2005 | Burns et al. ................ 73/170.02 |
| 7,383,131 | B1* | 6/2008 | Wey et al. ......................... 702/4 |
| 7,392,689 | B2* | 7/2008 | Kim et al. .................... 73/31.02 |
| 7,456,961 | B2* | 11/2008 | Barton et al. ................. 356/338 |
| 7,591,980 | B2 | 9/2009 | Call et al. |

(Continued)

FOREIGN PATENT DOCUMENTS

| DE | 4140406 A1 | 6/1993 |
| DE | 102007035678 A1 | 2/2009 |

OTHER PUBLICATIONS

Brenninkmeijer, C.A.M. et al, Civil Aircraft for the regular investigation of the atmosphere based on an instrumented container: The new CARIBIC system, Atmospheric Chemistry and Physics, 2007, vol. 7, pp. 4953-4976, Germany.

(Continued)

*Primary Examiner* — Thomas Black
*Assistant Examiner* — Peter D Nolan
(74) *Attorney, Agent, or Firm* — Ingrassia Fisher & Lorenz P.C.

(57) ABSTRACT

A measuring device for an aircraft is provided in order to determine physical properties of aerosol particles in real time. The device includes a heating device that separates volatile and solid aerosol particles, and a particle sensor that measures acquired data. The physical properties of the solid aerosol particles are determined with an analyzer. The determined analytical data is forwarded to other internal aircraft systems via a communication interface. Due to the formation of a measuring data or analytical data network with several airliners equipped with the measuring device, accurate and up-to-date information on the particle pollution, for example, along flight paths, can be obtained and used for defining no-fly zones, if so required.

15 Claims, 3 Drawing Sheets

(56) References Cited

U.S. PATENT DOCUMENTS

| | | | |
|---|---|---|---|
| 8,209,071 B2* | 6/2012 | Ross | 701/14 |
| 2004/0112123 A1* | 6/2004 | Fries et al. | 73/64.56 |
| 2012/0068862 A1* | 3/2012 | Tillotson | 340/963 |

OTHER PUBLICATIONS

Weigel, R, Ultrafeine Aerosolpartikel in der Stratohaere: Charakterisierung eines Kondensationskernzaehlers und in-situ-Messugen in polaren, mittleren and tropischen Breiten, Dissertation University Mainz, Nov. 2005.

International Searching Authority, International Search Report for PCT/EP2011059226, dated Sep. 5, 2011.

German Patent Office, German Office Action for German Patent Application No. 10 2010 022 673.4 dated Jun. 8, 2011.

\* cited by examiner

PARTICLE SENSOR FOR IN SITU ATMOSPHERIC MEASUREMENT

CROSS-REFERENCE TO RELATED APPLICATIONS

This is a continuation of International Application No. PCT/EP2011/059226, filed Jun. 3, 2011, which application claims priority to German Patent Application No. 10 2010 022 673.4, filed Jun. 4, 2010, and to U.S. Provisional Patent Application No. 61/351,588, filed Jun. 4, 2010, which are incorporated herein by reference in their entirety.

TECHNICAL FIELD

The present disclosure pertains to a measuring device for an aerosol analysis, an aircraft with a measuring device, a system with at least two aircraft-borne measuring devices and a ground station. The present disclosure also pertains to a method for an aerosol particle analysis and a computer program element, as well as a computer-readable storage medium.

BACKGROUND

Specially equipped measuring aircraft are used for identifying trace gases and aerosols in the atmosphere. The term aerosols refers to solid and/or liquid particles in the air. One distinguishes between aerosols in the form of Aitken particles with a size of less than about 0.1 μm and the so-called fine aerosols of the accumulation mode with sizes between about 0.1 μm and about 2.5 μm. Particles larger than about 2.5 μm are referred to as coarse aerosol. Solid dust particles can be created during the mechanical destruction of solid material and usually have diameters larger than about 1 μm. The most important sources for dust aerosols are desert and arid environments. Volcanic eruptions also emit about $33*10^6$ tons of aerosols annually into the atmosphere. The importance of volcanic dust results from the fact that a large quantity of dust aerosols and fly ash can be locally thrown into high altitudes of the atmosphere and therefore represent, if applicable, a hazard to air traffic. However, there is no wide-area warning system for volcanic ash or other hazard sources that can exist for air traffic due to high aerosol pollutions such as forest fires.

In order to survey the volcanic ash pollution above Europe due to the volcanic eruption on the Icelandic Eyjafella Glacier, measurements with the research aircraft of the German Aerospace Center were carried out in April and May of 2010. However, these measurements merely represent samples taken for a limited time and over a limited area. The data acquisition is carried out with the aid of measuring engineers rather than automatically. Subsequently, a time-consuming data evaluation of the measuring results is required on the ground. A fast and accurate warning of civil aviation, for example, about high particle concentrations in case of a nearby volcanic eruption cannot be realized based on the utilization of individual research aircraft. A single research aircraft can hardly survey a moving ash cloud that partly has a length or width of about 1000 km, as well as its exact boundaries, because the smoke cloud continuously changes and aging of the air masses takes place.

Ground-based Lidar systems and satellites are only reliable under cloudless conditions and therefore can frequently not be used as sole data source. However, exact predictions of the dispersion area of a concentrated smoke cloud are required in order to create purposeful no-fly zones. Large-scale no-fly zones resulting from the inaccuracy and the high expenditure of time of today's measuring methods can lead to significant economic losses. It is therefore necessary to provide a simple particle measuring system in order to minimize a restriction of air traffic.

In addition, other objects, desirable features and characteristics will become apparent from the subsequent summary and detailed description, and the appended claims, taken in conjunction with the accompanying drawings and this background.

SUMMARY

According to various aspects of the present disclosure, provided is an improved particle sensor for continuous real-time measurements for aircraft. In one of various embodiments, also provided is a method to use the results of the analysis of the particle sensor for improving air traffic safety.

According to an exemplary embodiment of the present disclosure, a measuring device for an aircraft is provided for determining the physical properties of aerosol particles in real time. The measuring device comprises a heating device that is designed for separating volatile and solid aerosol particles, a particle sensor for acquiring measuring data, an analyzer for determining the physical properties of the solid aerosol particles based on the acquired measuring data and a communication interface for forwarding the determined analytical data to other internal aircraft systems.

The heating device is suitable for transferring liquid or frozen water droplets into the gaseous phase such that the particle sensor can measure the mass concentration, quantity concentration or size distribution of the solid particles. The acquired data can be evaluated in-situ and forwarded to other internal aircraft systems via the communication interface. In this way, the analytical data of the particle sensor can be forwarded online to the pilot in the cockpit or to a central onboard computer.

According to another exemplary embodiment of the measuring device, the determined analytical data is selected from a group comprising: particle concentration, mass, size distribution, dispersion and absorption.

In this way, the physical and optical properties of the particles can be determined. Generally, the number density and size distribution can be used for a comparison with limiting values for safe flying. For example, the light absorption measured in the atmosphere or the presence of relatively large particles with a size, e.g., greater than about 10 μm of the coarse particle mode can be used as an indicator for fly ash.

According to another exemplary embodiment of the measuring device, the analyzer is designed for outputting a warning signal via the communication interface if a certain predefined limiting value with respect to the analytical data was exceeded.

In this way, the pilot of the aircraft equipped with the particle sensor can be warned when the aircraft enters an area that is polluted with particles, for example, due to a volcanic eruption or forest fire. If remote sensing techniques such as, for example, Lidar are used aboard the aircraft, a smoke plume can, for example, be surveyed from above and the pilot can be informed of the suitable flight altitudes for continuing the flight under the given conditions.

The warning signal is coupled to a limiting value that is defined by law or by an aircraft operator in order to ensure safe flying. The fact that the limiting value has been exceeded can also be quickly transmitted to an aircraft approaching the smoke plume in order to carry out possible flight corrections.

In this case, communication with air traffic control is required in order to ensure a large-scale coordination of the airliners.

According to another exemplary embodiment of the measuring device, the measuring device comprises an aerosol inlet, wherein the aerosol particles can be transported to the particle sensor by means of ram pressure or a conveying device.

If the inlet is directed forward, the ram pressure can be used for the sampling process. In longer inlet systems, a conveying device such as a pump may be required in order to ensure the sampling. The inlet system itself may be heated in order to ensure the separation of water droplets. In this respect, it needs to be observed that the measuring chamber temperature is chosen so high that no condensation of the water vapor takes place.

The measuring device may be realized such that it can be easily dismounted and mounted from/on the underside of airfoils or suitable pylons. In this case, it is advantageous that the sampling can be easily carried out by means of ram pressure, wherein the inlet system can directly collect the particles such that such that a deposition of the particles in long or curved inlet systems can be precluded.

It is furthermore possible to provide the measuring devices with inlet systems that require an opening in the skin of the aircraft. In inlets on the fuselage or ceiling, the sampling should not be disturbed by the boundary layer of the aircraft or aerodynamics. The inlet system may lead into a cargo compartment, in which racks can carry one or more measuring devices.

According to another exemplary embodiment of the measuring device, the particle sensor is selected from a group comprising: spectrometer, laser anemometer, mass spectrometer, condensation nucleus counter, absorption photometer and electrostatic sensor.

The laser-based sensors can survey the scattered light measured in the aerosol sample by means of photodetectors. Laser spectrometers or laser Doppler anemometers may be used as measuring technique. Doppler particle sensors utilize the Doppler effect for measuring particles. In this case, the particle size and speed is dependent on the wavelength of the laser and the optical configuration only. In this way, it is possible to measure without calibration. This measuring technique is furthermore suitable for the measurement with high number densities.

Condensation nucleus counters operate with a condensation fluid such as, for example, butanol and can determine the overall quantity concentration. The measuring principle is based on the particles absorbing butanol and therefore growing to several times their original size. This makes them visible to laser light and detectable.

Soot particles and their mass concentration can be continuously determined by measuring the absorption coefficient on a filter band.

An electrostatic sensor can determine the size distribution and number of ionized particles with specific aerodynamic diameters in accordance with their electromobility.

High sulfur dioxide or carbon monoxide concentrations can be measured, for example, in fresh volcanic clouds, with the aid of suitable trace gas sensors and used as indicator for an ash cloud. In this way, a mineral dust cloud from the Sahara can be easily distinguished from a volcanic ash cloud. These measuring devices can be combined with the particle measuring devices in an aircraft rack. A real-time measurement of the trace gases is usually possible. However, a few trace gas measuring systems require a calibration that, if so required, can be carried out on the ground prior to take-off or after landing.

The components such as carbon dioxide, ozone or nitrogen oxides can be detected as measuring parameters by means of physical or chemical measuring methods. The sensors are provided with suitable pumps, a calibration unit and control electronics. The spatial and temporal variability can be forwarded to a central database together with the data of the particle analysis. In this way, the chemical and physical processes taking place in a smoke plume can be mapped.

According to another exemplary embodiment of the present disclosure, an aircraft with a measuring device is provided that features a navigation system for determining the location information of the aircraft, a central onboard computer for acquiring and additionally processing data and a communication system for transmitting data to ground stations and/or other aircraft. In this case, the central onboard computer is designed for calculating the analytical data of the measuring device in dependence on the location information of the aircraft.

The spatial variability of the measurements can be illustrated based on the exact navigation data or location information of the aircraft. The time resolution may, for example, amount to about 1 Hz in order to exactly illustrate the spatial and temporal variability in the air space. If the measuring devices are used aboard airliners, several measuring results can be simultaneously forwarded to a central database via an external communication network. Alternatively, the aircraft may also communicate with one another in order to warn the following flight in a timely fashion when a limiting value is exceeded.

According to another exemplary embodiment of the present disclosure, a system with an aircraft-borne measuring device is provided that comprises at least one other aircraft-borne measuring device. In this case, the at least two measuring devices are designed for sending location-dependent and time-dependent analytical data to a central ground station by means of a communication interface, wherein a three-dimensional particle distribution in the air space can be calculated in a central database of the ground station based on the received analytical data.

A wide-area warning system along flight paths can be ensured due to the fact that the measuring devices are simultaneously installed in several airliners and the acquired analytical data can be wirelessly received by a ground station with a central database. The location-dependent and time-dependent analytical data can serve as the basis for a three-dimensional particle concentration map in order to directly make available this data to the air traffic control or the pilots. Since the in-situ measurements are carried out in real time, current hazardous areas or no-fly zones can be determined. Consequently, it is possible to reduce a possible no-fly zone of the air space to a minimum.

According to another exemplary embodiment of the present disclosure, a system is provided, wherein a ground station furthermore receives basic meteorological data from the aircraft and/or operational services or research platforms in order to predict the three-dimensional particle distribution.

In order to also determine, in one example, the three-dimensional distribution over a wide area beyond the flight paths, an interpolation of the analytical data with consideration of basic meteorological data is required. The air mass movement can be determined with the aid of the wind speed and other parameters. For this purpose, the data measured aboard can be used or the current databases of operational services such as the national weather service (in Germany, for example: German Weather Service DWD) can be accessed. Areas of rain can, for example, lead to the particle concentration being significantly reduced due to particles being washed out. Global transport models, trajectories or particle dispersion models can also be incorporated in order to provide three-dimensional maps. In addition, communication links with research institutes or the ground measuring systems such as Lidar systems can be used for providing the entire altitude profile, namely also outside conventional airports. Measuring aircraft, balloon probes, ground stations and national or international research institutes may be considered as research platforms.

According to another exemplary embodiment of the present disclosure, a method for an aerosol particle analysis can comprise: heating the inlet and/or the measuring chamber for transferring the liquid water into the vapor phase, acquiring aerosol particle measuring data, determining the physical properties of the solid aerosol particles based on the acquired measuring data and forwarding the analytical data to other internal aircraft systems via a communication interface. This method furthermore comprises comparing the analytical data with predefined limiting values and issuing a warning signal to the cockpit in case a limiting value is exceeded.

In this way, the measuring sensor technology can be directly and immediately utilized for protecting the individual aircraft when a limiting value of particle parameters is exceeded. This can improve the safety of the aircraft, for example, during unpredictable volcanic eruptions. On average, one volcano erupts somewhere in the world every week.

According to another exemplary embodiment of the present disclosure, a method for an aerosol particle analysis is disclosed that furthermore comprises: transmitting the analytical data of measuring devices of a plurality of aircraft to a central database of a ground station via a wireless communication device and establishing a three-dimensional particle distribution based on the collected analytical data and with consideration of meteorological data.

Due to the formation of a measuring data or analytical data network comprising several airliners that are respectively equipped with a particle sensor, it is possible to obtain accurate and up-to-date information on the particle pollution, for example, along flight paths. Additional calculations can be carried out in a central database on the ground with the aid of this extensive measuring data. The data measured in-situ is prepared such that it can be quickly and easily transmitted by means of telemetry. In this respect, a global availability, e.g., via the Internet would also be conceivable or satellite communication paths can be used. The pooling of the data in a central database also allows the utilization of data of other ground stations or research institutes.

According to another exemplary embodiment of the present disclosure, a method is disclosed that can furthermore define no-fly zones when limiting values are exceeded based on the three-dimensional time-dependent and location-dependent particle distribution.

The three-dimensional particle distributions can also be used as the basis for blocking or releasing airspace. In this case, the instructions or warnings or detours can be transmitted to the pilots via wireless communication like the measuring results. In this respect, a cooperation with air traffic control is also possible.

According to another exemplary embodiment of the present disclosure, a computer program element is provided that, if it is executed by a processor, instructs the processor to carry out the above-described method.

According to another exemplary embodiment of the present disclosure, a machine-readable storage medium is provided, on which a computer program element is stored that, if it is executed on a processor, instructs the processor to carry out the above-described method.

A person skilled in the art can gather other characteristics and advantages of the disclosure from the following description of exemplary embodiments that refers to the attached drawings, wherein the described exemplary embodiments should not be interpreted in a restrictive sense.

BRIEF DESCRIPTION OF THE DRAWINGS

The various embodiments will hereinafter be described in conjunction with the following drawing figures, wherein like numerals denote like elements, and wherein.

DETAILED DESCRIPTION

The following detailed description is merely exemplary in nature and is not intended to limit the present disclosure or the application and uses of the present disclosure. Furthermore, there is no intention to be bound by any theory presented in the preceding background or the following detailed description.

Figure 1:
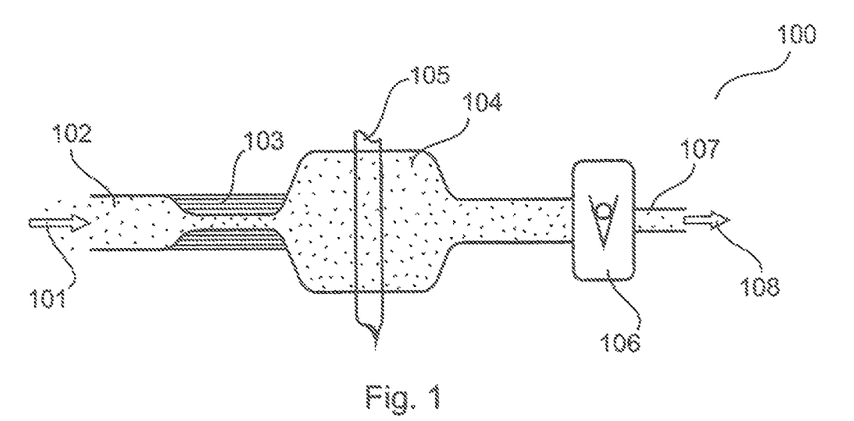
FIG. 1 shows a schematic representation of a particle measuring device according to one exemplary embodiment of the present disclosure.

FIG. 1 shows a measuring device 100 with an inlet 102 that is designed for transporting the aerosol air sample 101 to the measuring chamber 104 by means of ram pressure. This means that the input is directed forward. This measuring device can, for example, be easily mounted on a (not-shown) pylon underneath the airfoil.

A heating device 103 is arranged upstream of the measuring chamber 104 in order to separate solid from liquid particles. The evaporation may take place, for example, at temperatures of approximately about 100° C. At higher altitudes, ice particles may also be present and transferred into the vapor phase by the heating step. The measurement of the particles is carried out with an optical method, for example, a laser beam 105. The volumetric flow rate of the gas sample is determined with a suitable flowmeter 106. The outlet system 107 once again channels the measured air 108 outward.

It would also be possible to install the heating device between two measuring chambers in order to determine the particle concentration with and without the separation of liquid particles. In addition to the solid ash dust, sulfate aerosols that occur, in one example, during volcanic eruptions can also be measured as typical aerosols.

The measuring device 100 illustrated in FIG. 1 can be installed in a housing or in a so-called "wing pod" together with other measuring devices. These housings or "wing pods" can be easily mounted on the airfoils of the aircraft. If the design is approved for an aircraft type, they can be quickly utilized on demand in scheduled flight operations. Relatively small laser measuring devices can be cost-efficiently provided for in-situ particle measurements.

If space for several measuring devices is available, it would be possible, for example, to utilize one measuring device for the size distribution of the coarse particles and another device for the particles in the accumulation mode. The spatial and temporal distribution of the atmospheric aerosol can be determined with the aid of the analytical data acquired with the measuring devices such as, for example, the particle quantity and size distribution in combination with the location information of the aircraft in order to evaluate its potential local and global hazards in-situ.

Figure 2:
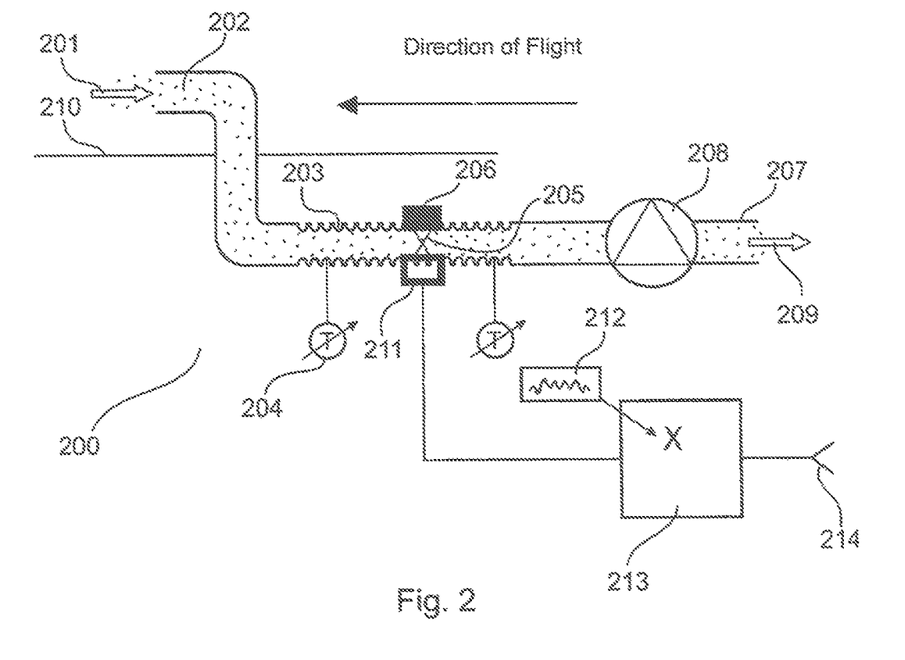
FIG. 2 shows a schematic representation of another exemplary embodiment of a particle measuring device.

FIG. 2 schematically shows another exemplary embodiment of a measuring device 200. The inlet 202 may be installed, for example, on the aircraft ceiling (upper aircraft skin 210) in a suitable opening. In the example shown, the inlet is directed forward. i.e., in the direction of flight (see arrow). The removal of a partial stream of the sample gas 201 is realized with a pump 208. The inlet should protrude over the skin to such a degree that the sampling is not influenced by the aircraft boundary layer. The heating device 203 is realized in the form of a pipe system heater, in this exemplary embodiment. The adjusted temperature can be monitored with suitable temperature sensors 204.

The measuring device is based on an optical system, in which two laser beams 205 are directed at a sampling section by a device 206. The measurements are carried out at the intersecting point of the two beams. The particles contained in the sample scatter the light. Measuring detectors 211 measure the scattering signals and the analyzer 213 can calculate a particle size distribution or number density by means of suitable signal processing such as a pulse height analysis 212. The analytical data can be forwarded to another aircraft system such as the (not-shown) onboard computer via a communication interface, e.g., a transceiver 214.

The measuring data can either be compared with limiting values in the onboard computer or in the analyzer 213. If a limiting value is exceeded, a warning signal can be directly transmitted into the cockpit.

The measured sample air 209 is channeled away through an outlet system 207. This outlet may also be arranged in another opening of the skin. In this way, the air heated by the heating device is not transported into an interior of the aircraft, but rather discharged into the outside air.

Figure 3:
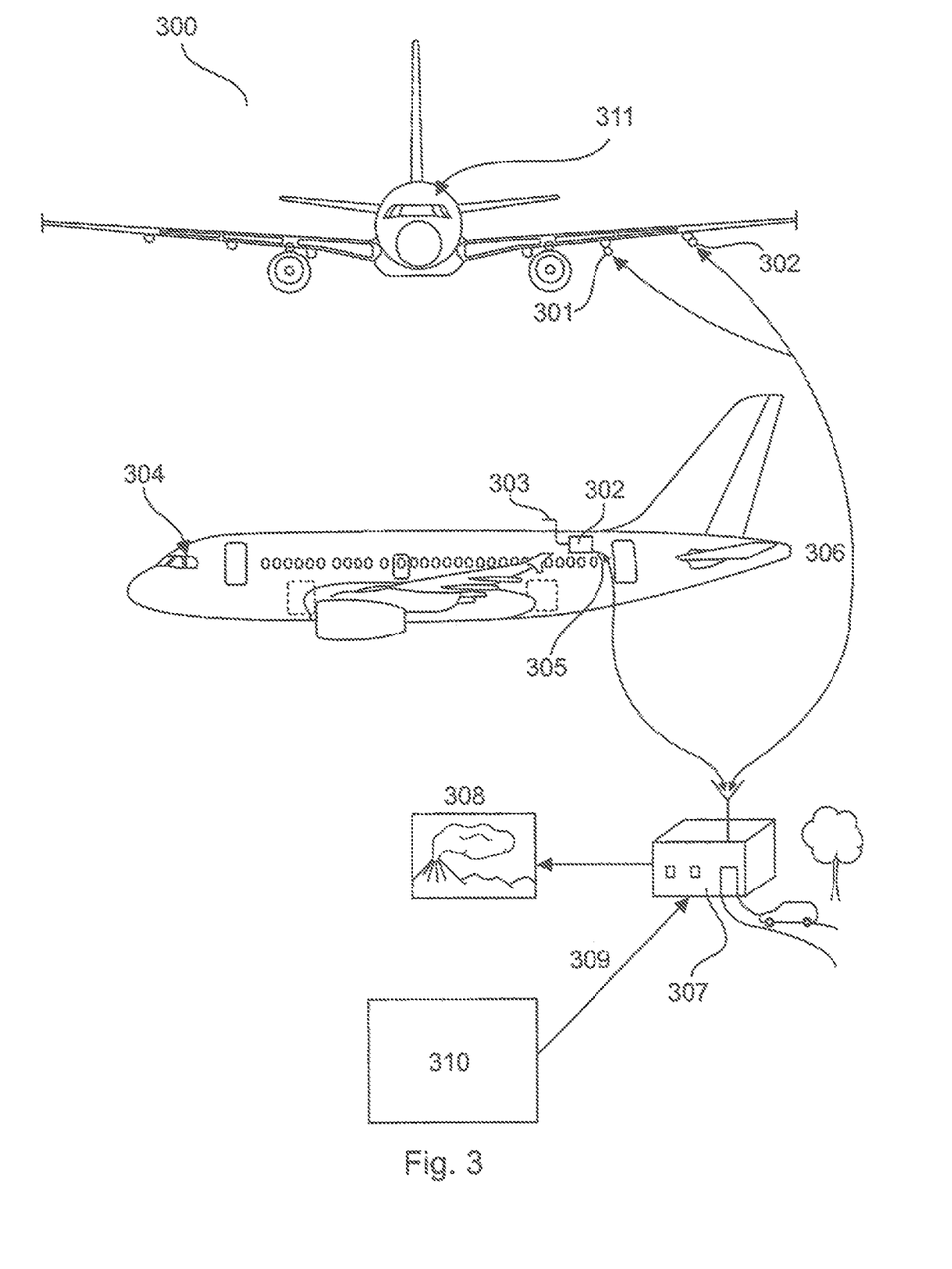
FIG. 3 shows a system of two aircraft with measuring devices and a ground station with a central database according to another exemplary embodiment of the present disclosure.

FIG. 3 shows a system 300 of two aircraft 311, 304 with measuring devices 301, 302 and a ground station 307 with a central database according to another exemplary embodiment of the present disclosure. The two aircraft 304, 311 shown are merely illustrated as examples for a plurality of aircraft. The measuring devices 301 and 302 are realized in the form of measuring probes underneath the airfoil. The measuring device 302 may, for example, measure the coarse particle fraction while the measuring device 301 measures the fine particles. In one example, the larger particles can be assumed to be indicators for recent smoke plumes, for example, of volcanoes because larger particles usually remain in the atmosphere for a shorter period of time than finer particles.

An identical particle sensor 302 is installed in the aircraft 304 that can be used as a normal passenger or cargo aircraft like the aircraft 311. In this case, the sampling takes place through an opening in the ceiling of the aircraft 304. The inlet 303 is oriented in the direction of flight in order to capture all particles. The measuring device 302 is accommodated, for example, in a cargo compartment. The measuring device may be installed in a rack. This rack may also contain other measuring devices and components for measuring other particle fractions or with different temperature ranges in order to separate volatile fractions such as liquid water or sulfuric acid in stages. In addition, variables such as soot or trace gases such as sulfur dioxide, carbon monoxide, ozone or nitrogen oxides can be measured. Suitable mass spectrometers can also determine the chemical composition of the aerosols. In addition, the measuring device can be supplemented with discontinuous measuring methods such as the collection of particles on filters. These filters can be chemically analyzed at a later time.

The analytical data can be transmitted to a ground station 307 via a wireless communication device 306 (see double arrows). The ground station is equipped with a central database that can collect the measuring data of all aircraft equipped with measuring devices 302. Supplementary modeling tools such as trajectories or global transport models make it possible to determine three-dimensional particle concentration distributions, for example, of a volcanic smoke plume 308 based on the analytical data. The database can also access other operational services 310 of national or international centers for predictions or for covering the spaces beyond flight paths. These operational services include, for example, the German Weather Service (DWD) in Germany or the international organization European Center for Medium-Range Weather Forecasts (ECMWF). In addition, up-to-date basic meteorological data can also be transmitted by the aircraft.

The determined spatial and temporal distributions of the particle pollution can be compared with predefined limiting values and, if applicable, no-fly zones for limited areas can subsequently be forwarded to the air traffic control.

Figure 4:
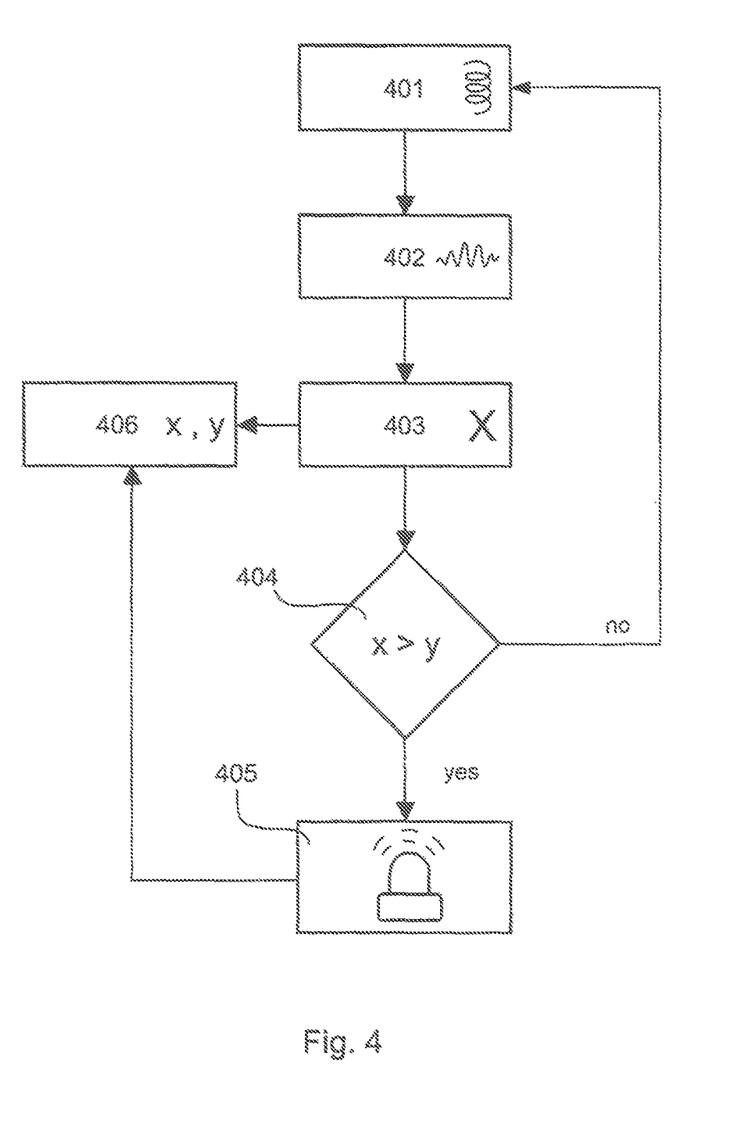
FIG. 4 shows a flow chart of the method according to another exemplary embodiment of the present disclosure.

FIG. 4 shows a flow chart of a method for an aerosol particle analysis. In 401, sampling air is heated in order to transfer water from the liquid or ice phase into the vapor phase. In 402, the aerosol particle measuring data is acquired. This can be realized, for example, with an optical method, wherein the measuring data of a spectrometer can be illustrated in the form of a spectrum. This measuring data is analyzed in 403 such that the physical properties of the solid aerosol particles can be calculated. This analytical data can be transmitted to another internal aircraft system such as the onboard computer in a wire-bound or wireless fashion in 406.

If it is determined that a limiting value y was exceeded in 404, in which the determined value x is compared with the predefined limiting value y, a warning signal is output in 405. This warning signal can be individually used by the aircraft pilot after it was transmitted to the cockpit like in 406.

The data collected aboard in real time can be incorporated into a system that is composed of a ground station and/or a plurality of aircraft. In this way, a plurality of particle measuring data can be centrally collected in a ground station and spatial and temporal distributions can be subsequently calculated. These three-dimensional distributions can be used as the basis for possible air traffic control measures. In this case, a fast and global communication system forms the basis for an up-to-date warning system when limiting values are exceeded. Due to this method, an up-to-date evaluation of extreme situations such as volcanic eruptions can be carried out on short notice. In this way, it is possible to better organize no-fly zones and to minimize economic losses.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the present disclosure in any way. Rather, the foregoing detailed description will provide those skilled in the art with a convenient road map for implementing an exemplary embodiment, it being understood that various changes may be made in the function and arrangement of elements described in an exemplary embodiment without departing from the scope of the present disclosure as set forth in the appended claims and their legal equivalents.

What is claimed is:

1. A system for calculating a three-dimensional particle distribution in an air space, comprising:
   an inlet for sampling particles in the air space;
   a first aircraft-borne measuring device for determining physical properties of aerosol particles, the physical properties of the aerosol particles including at least a mass of the aerosol particles, and the first aircraft-borne measuring device generates first location-dependent and time-dependent analytical data, the first measuring device comprising a heating device that separates volatile and solid aerosol particles;
   at least one second aircraft-borne measuring device for determining physical properties of aerosol particles, and the at least one second aircraft-borne measuring device generates second location-dependent and time-dependent analytical data;
   wherein the first aircraft-borne measuring device and the at least one second aircraft-borne measuring device send the first location-dependent and time-dependent analytical data and second location-dependent and time-dependent analytical data to a central ground station by means of a communication interface, and the three-dimensional particle distribution in the air space is calculated in the central database of the ground station based on the received analytical data.

2. The system of claim 1, wherein the determined physical properties further comprise:
   particle concentration;
   size distribution;
   dispersion;
   absorption; and
   combinations thereof.

3. The system of claim 1, the first measuring device further comprising:
   a particle sensor that acquires measuring data;
   an analyzer that determines the physical properties of the solid aerosol particles based on the acquired measuring data and outputs analytical data; and
   a communication interface that forwards the determined analytical data to other internal aircraft systems.

4. The system of claim 3, wherein the analyzer outputs a warning signal via the communication interface when a certain predefined limiting value with respect to the analytical data is exceeded.

5. The system of claim 3, wherein the first measuring device further comprises:
   an aerosol inlet, wherein the aerosol particles are transported to the particle sensor by ram pressure or a conveying device.

6. The system of claim 3, wherein the particle sensor is selected from a group comprising:
   a spectrometer;
   a laser anemometer;
   a mass spectrometer;
   a condensation nucleus counter;
   an absorption photometer; and
   an electrostatic sensor.

7. The system of claim 3, wherein the first measuring device further comprises:
   a sensor that determines chemical parameters of a measured gas.

8. The system of claim 1, further comprising an aircraft, which comprises:
   a navigation system for determining the location information of the aircraft;
   a central onboard computer for acquiring and additionally processing data; and
   a communication system for transmitting data to ground stations and/or other aircraft.

9. The system of claim 1, wherein the ground station further receives basic meteorological data from at least one of an aircraft, an operational services and a research platform in order to predict the three-dimensional particle distribution.

10. A method for an aerosol particle analysis, comprising:
    sampling aerosol particles using an aircraft-borne inlet
    determining physical properties of aerosol particles with a first aircraft-borne measuring device, the physical properties of the aerosol particles including at least a particle concentration and a mass of the aerosol particles, the first aircraft-borne measuring device generating first location-dependent and time-dependent analytical data, the first measuring device comprising a heating device that separates volatile and solid aerosol particles;
    determining physical properties of aerosol particles with at least one second aircraft-borne measuring device, the at least one second aircraft-borne measuring device generating second location-dependent and time-dependent analytical data;
    transmitting the first and second location-dependent and time-dependent analytical data from a plurality of aircraft to a central database of a ground station via a wireless communication device; and
    calculating a three-dimensional particle distribution of the aerosol particles in an airspace based on the collected analytical data.

11. The method of claim 10, further comprising:
    comparing the determined physical properties with predefined limiting values; and
    outputting a warning signal to a cockpit in case a limiting value is exceeded.

12. The method of claim 10, further comprising:
    defining no-fly zones when limiting values are exceeded based on the three-dimensional particle distribution.

13. A computer program product, comprising:
    a tangible storage medium readable by a processor and storing instructions for execution by the processor for performing a method comprising:
    sampling aerosol particles using an aircraft-borne inlet
    determining physical properties of aerosol particles with a first aircraft-borne measuring device, the first aircraft-borne measuring device generates first location-dependent and time-dependent analytical data, the first measuring device comprising a heating device that separates volatile and solid aerosol particles;
    determining physical properties of aerosol particles with at least one second aircraft-borne measuring device, the at least one second aircraft-borne measuring device generates second location-dependent and time-dependent analytical data;
    transmitting the first and second location-dependent and time-dependent analytical data from a plurality of aircraft to a central database of a ground station via a wireless communication device; and
    calculating a three-dimensional particle distribution in an air space based on the collected analytical data,
    wherein the physical properties of the aerosol particles includes at least one of a mass of the aerosol particles, a size distribution of the aerosol particles, a dispersion of the aerosol particles, an absorption of the aerosol particles and combinations thereof.

14. The computer program product of claim 13, wherein the method further comprises:
- comparing the determined physical properties with predefined limiting values; and
- outputting a warning signal to a cockpit in case a limiting value is exceeded.

15. The computer program product of claim 13, wherein the method further comprises:
- defining no-fly zones when limiting values are exceeded based on the three-dimensional particle distribution.

* * * * *